United States Patent
Susami et al.

(10) Patent No.: US 6,700,949 B2
(45) Date of Patent: Mar. 2, 2004

(54) RETRACTABLE COLLIMATOR APPARATUS FOR A CT-PET SYSTEM

(75) Inventors: Larry Susami, Waukesha, WI (US); Michael Dale Maki, Oconomowoc, WI (US); Thomas Robert Schaefer, Germantown, WI (US)

(73) Assignee: GE Medical Systems Global Technology LLC, Waukesha, WI (US)

( * ) Notice: Subject to any disclaimer, the term of this patent is extended or adjusted under 35 U.S.C. 154(b) by 0 days.

(21) Appl. No.: 09/962,868

(22) Filed: Sep. 25, 2001

(65) Prior Publication Data
US 2003/0058984 A1 Mar. 27, 2003

(51) Int. Cl.⁷ .................................................. H05G 1/60
(52) U.S. Cl. ................................ 378/19; 378/4; 378/20; 378/11; 378/145; 378/147; 378/195; 250/363.03; 250/363.1
(58) Field of Search ................................ 378/19, 4, 20, 378/11, 145, 147, 195–198; 250/363.03, 363.1

(56) References Cited

U.S. PATENT DOCUMENTS 5,059,799 A * 10/1991 Kurakake ............... 250/363.1
5,703,369 A * 12/1997 Mori ..................... 250/363.03

* cited by examiner

Primary Examiner—Robert H. Kim
Assistant Examiner—George Wang
(74) Attorney, Agent, or Firm—Quarles & Brady, LLP; Carl Horton

(57) ABSTRACT

An apparatus for use with a combined CT-PET system wherein a CT source and detector are mounted to a front end of a CT support and the support forms a parking space about a translation axis, a PET detector is mounted to a rear end of the support and a collimator support extends from the PET detector at least part way into the parking space, a collimator is mounted to the collimator support for movement between first and second positions inside the PET detector and outside the PET detector and at least partially within the parking space, respectively, a radiation blocking shield is mounted to the PET detector opposite the CT support to block radiation from that direction from being detected by the PET detector.

19 Claims, 4 Drawing Sheets

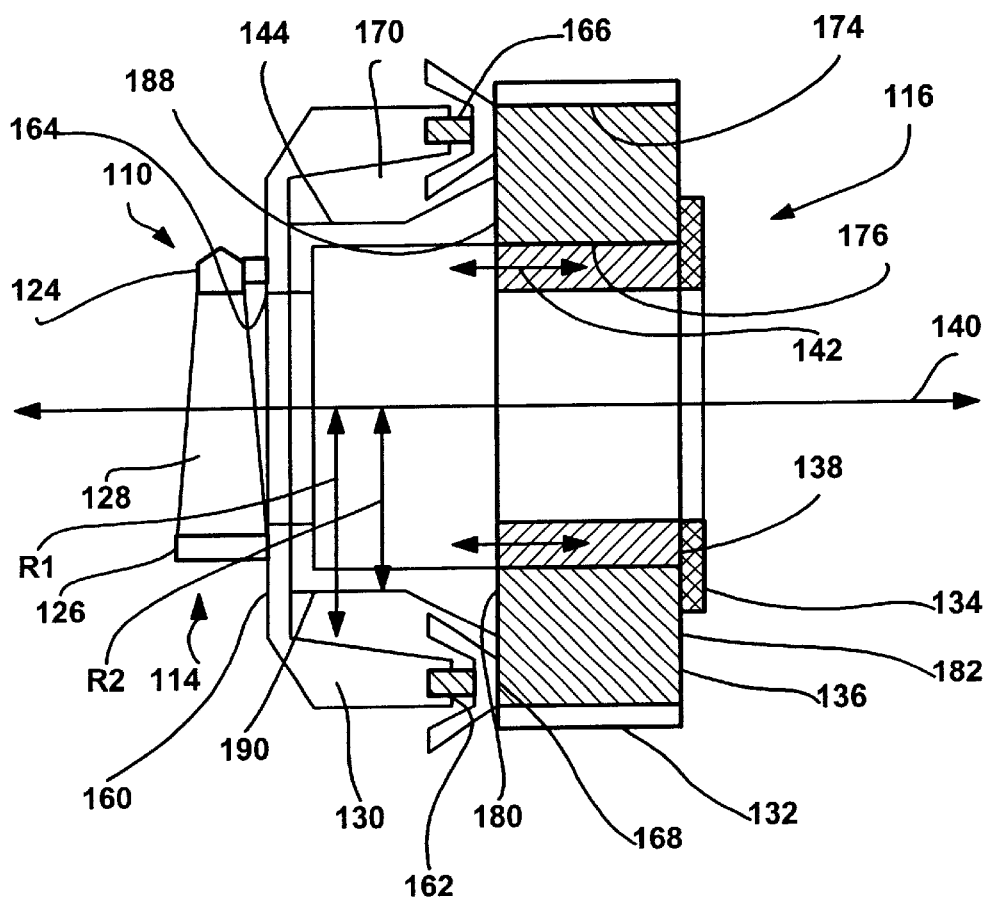

RETRACTABLE COLLIMATOR APPARATUS FOR A CT-PET SYSTEM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The field of the invention is medical imaging and more particularly collimator apparatus to be used in combined imaging modality systems and still more particularly retractable PET collimator apparatus for use in combined CT-PET systems.

Throughout this specification, in the interest of simplifying this explanation, an organ to be imaged will be referred to generally as an "organ of interest" and prior art and the invention will be described with respect to a hypothetical organ of interest. In addition, the phrase "translation axis" will be used to refer to an axis along which a patient is translated through an imaging system during data acquisition.

The medical imaging industry has developed many different types of imaging systems that are useful for diagnostic purposes. Two of the more widely used systems include computerized tomography (CT) systems and positron emission tomography (PET) systems.

In CT systems, an x-ray source projects a fan-shaped beam which is collimated to lie within an X-Y plane of a Cartesian coordinate system, termed the "CT imaging plane." The x-ray beam passes through an organ of interest, such as the torso of a patient, and impinges upon an array of radiation detectors. The intensity of the transmitted radiation is dependent upon the attenuation of the x-ray beam by the organ of interest and each detector produces a separate electrical signal that is a measurement of the beam attenuation. The attenuation measurements from all the detectors are acquired separately to produce a transmission profile.

Third generation CT systems include a base support for supporting the CT source and detector for rotation about the translation axis. To accommodate system tilt and reduce the overall system height and width dimensions, the source and detector are typically mounted axially along the translation axis with respect to the base support via a slip ring that provides power to the source and detector and also provides a data bus for transferring collected data to an image processor and archive.

In third generation CT systems the source and detector are rotated on the base support within the imaging plane and around the organ of interest so that the angle at which the x-ray beam intersects the organ constantly changes. A group of x-ray attenuation measurements from the detector array at a given angle is referred to as a "view" and a "scan" of the object comprises a set of views made at different angular orientations during one revolution of the x-ray source and detector. Using various data collection and manipulation techniques CT data can be used to generate two and three dimensional images of the organ of interest.

Unlike CT systems that rely on an external X-ray source to generate image data, PET systems rely on an energy source that resides within an organ of interest. To this end, positrons are positively charged electrons which are emitted by radio nuclides that have been prepared using a cyclotron or other device. The radio nuclides most often employed in diagnostic imaging are fluorine-18, carbon-11, nitrogen-13 and oxygen-15. Radio nuclides are employed as radioactive tracers called "radiopharmaceuticals" by incorporating them into substances such as glucose or carbon dioxide.

To use a radiopharmaceutical in PET imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmaceuticals will not be absorbed by a vessel wall. Thus, to image a specific organ or interest, a radiopharmaceutical known to accumulate either within the organ of interest or within a fluid that passes through the organ of interest can be selected. The process of concentrating often involves processes such as glucose metabolism, fatty acid metabolism and protein synthesis.

After the radiopharmaceutical becomes concentrated within an organ of interest and while the radio nuclides decay, the radio nuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using photon emission tomography (PET). First, each gamma ray has an energy of essentially 511 keV upon annihilation. Second, the two gamma rays are directed in substantially opposite directions.

In PET imaging, if the general locations of annihilations can be identified in three dimensions, a three dimensional image of an organ of interest can be reconstructed for observation. To detect annihilation locations, a PET camera is employed. An exemplary PET camera includes a plurality of detectors and a processor which, among other things, includes coincidence detection circuitry. For the purposes of this explanation it will be assumed that a PET camera includes detectors that are arranged to form an annular gantry about a PET imaging area. Each time an approximatly 511 keV photon impacts a detector, the detector generates an electronic signal or pulse which is provided to the processor coincidence circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes millions of annihilations are recorded, each annihilation associated with a unique detector pair. After an acquisition period, recorded annihilation data can be used via any of several different well known back projection procedures to construct images of the organ of interest.

In the case of PET systems, PET data can be collected simultaneously from a volume within an object of interest so that a 3D image can be generated. While there are several advantages to generating 3D images, many diagnostic requirements do not require such complex images and in these cases two dimensional "slice" images are sufficient.

Where 2D images will suffice, 2D images are preferred as the time required to acquire data needed to generate two dimensional images is less than that required to acquire data to generate three dimensional images. In addition to increasing system throughput (i.e., the number of imaging sessions that can be completed within a day), faster acquisition times increase patient comfort (i.e., reduce time during which patient must remain still) and, because the duration over which a patient must remain still is minimized, often result in images having reduces artifacts (i.e., the likelihood of patient movement is reduced as the acquisition time is shortened). In addition to reducing acquisition time, 2D data processing algorithms are simpler than 3D algorithms and processing procedures are therefore expedited.

In order to increase system versatility many conventional PET systems are capable of both 2D and 3D data acquisition. To this end a collimator is provided that is capable of restricting photons that pass through to a PET detector to within a series of parallel and adjacent planes. When 2D acquisition is required the collimator is positioned between the object of interest and the PET detector. When 3D acquisition is required the collimator is removed from between the object and detector.

In most PET systems that include a collimator, a collimator support is attached to the annular PET gantry axially along the translation axis. Thus, during 2D data acquisition the collimator is positioned within the gantry and during 3D acquisition the collimator is displaced outside the gantry and supported by the collimator support adjacent the gantry.

Each of the different imaging modalities typically has uses for which it is particularly advantageous. For example, CT systems that employ X-rays are useful for generating static images of bone and the like while PET systems are useful for generating dynamic or functional images of dynamic occurrences such as blood flow and the like.

For various reasons, in some diagnostic applications, it is advantageous to generate images that include both static and functional characteristics. To this end, one solution has been to sequentially use separate imaging systems to gather both functional and static imaging data sets and then combine those sets or corresponding images to generate unified functional/static images. For example, a CT system may be used to generate a CT image and subsequently a PET system may be used to generate a PET image, the two images being combined thereafter to generate the unified image.

Unfortunately, where unified images are required, several configuration and processing problems have to be overcome. First, after functional and dynamic image data has been collected, there has to be some way to align the functional and dynamic images so that the unified image precisely reflects relative anatomical positions. To this end, in some cases, fiducial markers have been employed. For example, a metallic button with a positron emitter can be placed on the surface of a patient's skin which is detectable by both the CT and PET systems. By aligning the marker in the resulting images the images can be aligned.

Second, where two separate imaging configurations are employed a patient has to be moved from one configuration to the next between acquisition sessions. Movement increases the likelihood that the patient's positions during the two imaging sessions will change thus tending to reduce the possibility of accurate alignment (i.e., relative positions of organs or the like could change during movement). The possibility of misalignment is exacerbated by the fact that often imaging session schedules will not allow both CT and PET imaging processes to be performed during the same day. Thus, overall diagnostic value of the resulting unified image can be reduced appreciably through movement between acquisition periods.

One solution to eliminate the need to move patient's between acquisition periods is to provide a dual CT-PET imaging system. Referring to FIG. 2, one exemplary CT-PET system 10 includes both a CT imaging configuration 14 and a PET imaging configuration 16 arranged sequentially along a single translation axis 40 with their relative positions fixed. In FIG. 2 the CT system 14 includes a CT base support 30, a CT source 24 and a CT detector 26, source 24 and detector 26 mounted to support 30 for rotation about axis 40. Source 24 generates fan beam 28 that is directed at detector 26.

Among other components, PET system 16 includes an annular PET detector 36 mounted in a detector gantry 32, a PET collimator 38 and a collimator support 44. As illustrated, collimator 38 is in the parked position supported outside detector 38 by support 44. collimator 38 is moveable into and out of detector 36 along the arrows collectively identified by numeral 42.

A support 20 for a support table 12 is positioned adjacent the system 10 with the table 12 moveable along translation axis 40. Here CT and PET systems 14, 16, respectively, can be used simultaneously or sequentially to acquire both CT and PET sets of imaging data in a relatively short time and without moving the patient from one imaging system to another. The end result is less patient movement, less time to gather required data and better alignment of resulting images to provide a more accurate unified image. Unfortunately, despite their advantages, dual CT-PET systems also have several shortcomings.

First, CT X-rays often scatter within an imaging area and, where not properly shielded, can be detected by an adjacent PET detector thereby rendering collected PET data essentially useless for diagnostic purposes. To overcome this problem, referring again to FIG. 2, a PET detector 36 in a combined CT-PET system can be equipped with a first lead shield 34 between the CT system 14 and the PET detector 36. In addition, because X-rays often bounce around an imaging room, a second lead shield is often provided on a side of the PET detector 36 opposite the first shield 34 to minimize detection of stray X-rays. In the cases where a PET detector includes a collimator 38, the collimator 38 may operate as the second lead shield so that only a single lead shield, in addition to the collimator, is required.

Second, dual imaging systems often require relatively long imaging bore lengths. Referring yet again to FIG. 2, the bore length D1 is the system length along translation axis 40 and includes adjacent segments required to accommodate each of a CT imaging area, (i.e., CT source 24 and detector 26 in the same trans-axial planar space), CT base support 30, PET detector gantry 32 and PET collimator support 44. In addition to requiring a large space in radiology departments, extended bore lengths can cause patients mental anguish as most patients are relatively unfamiliar with complex imaging systems and therefore most patients experience at least some anxiety while being translated through an imaging system bore. In addition to being unhealthy for the patient, mental anguish can also have an effect on imaging quality as anxiety often leads to patient movement.

Moreover, because the translation axis 40 is relatively long, support table 12 needs to extend a relatively long distance in order to accommodate the system configuration. While every effort is made to provide stiff supports and tables so that vertical alignment within CT and PET imaging areas can be maintained, when a patient is positioned on a table and the table is extended to accommodate the axial length of dual imaging systems, it has been found that the tables often sag such that the CT and PET data sets collected are mis-aligned along the translation axis 40. Exacerbating matters is the fact that over time stiffness of some supports and tables has been known to deteriorate. While stiffer tables and supports are an option, increased stiffness is a relatively expensive proposition as exotic configurations and materials have to be used to achieve greater stiffness.

Third, referring again to FIG. 2, because of the need for both of the CT base support 30 and the lead shield 34 between the CT and PET detectors 26, 38, respectively, there is a relatively large distance between the CT and PET imaging areas which results in increased acquisition times. Once again, longer acquisition times increase patient discomfort and therefore often result in patient movement and hence image artifacts.

BRIEF SUMMARY OF THE INVENTION

It has been recognized that the CT base support defines an essentially unused annular space between the CT imaging area and the PET gantry. It has also been recognized that with only minimal modifications to the collimator support, the collimator support can fit within the unused annular space. Thus, it has been recognized that the overall bore length in a dual CT-PET system can be reduced by modifying the relative positions of the CT imaging area, collimator support, PET gantry and lead shields so that the collimator support is positioned within the annular space and the collimator can be parked within the annular space during 3D image data acquisition. To this end, an exemplary embodiment of the invention includes a CT source and detector, a CT support having front and rear oppositely facing ends, the source and detector mounted to the front end so as to oppose each other and for rotation about a translation axis passing through a CT imaging area, the CT support also forming an annular parking space axially adjacent along the translation axis to the CT imaging area, an annular PET detector having front and rear oppositely facing ends, the PET detector positioned such that the front end of the PET detector is adjacent the rear end of the CT support and an annular collimator mounted to the PET detector for movement between a first position wherein the collimator is disposed within the PET detector and a second position wherein the collimator is outside the PET detector and at least partially within the parking space.

At least some embodiments include a collimator support mounted to the PET detector and extending from the front end of the PET detector at least part way into the parking space and the collimator is mounted to the collimator support for movement. Here the collimator support is typically mounted to the front end of the PET detector. The support may include rails and in that case the collimator would be mounted for movement along the rails.

Some embodiments further include a radiation shield mounted to the second end of the PET detector. This shield is provided to block stray radiation from entering the Pet detector from the side of the PET detector opposite the CT imaging area. On the side of the PET detector facing the CT imaging area the PET collimator operates to block stray radiation. When the collimator is positioned within the PET gantry during 3D acquisition, a wall of the collimator facing the CT imaging area operates to block stray radiation and when the collimator is positioned in the parking space during 2D acquisition, a wall of the collimator facing opposite the CT imaging area operates to block stray radiation.

In addition to accommodating placement of the collimator support and parked collimator within the parking space, by moving the stationary radiation detector to the side of the PET gantry opposite the CT imaging system, the bore length between oppositely the CT and PET imaging planes is reduced by at least the width of the radiation shield which results in faster data acquisition sessions (i.e., faster throughput), greater patient comfort and higher quality images.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE SEVERAL VIEWS OF THE DRAWINGS

FIG. 4 is a more detailed schematic diagram of the system of FIG. 3 in partial cross-section.

DETAILED DESCRIPTION OF THE INVENTION

Figure 1:
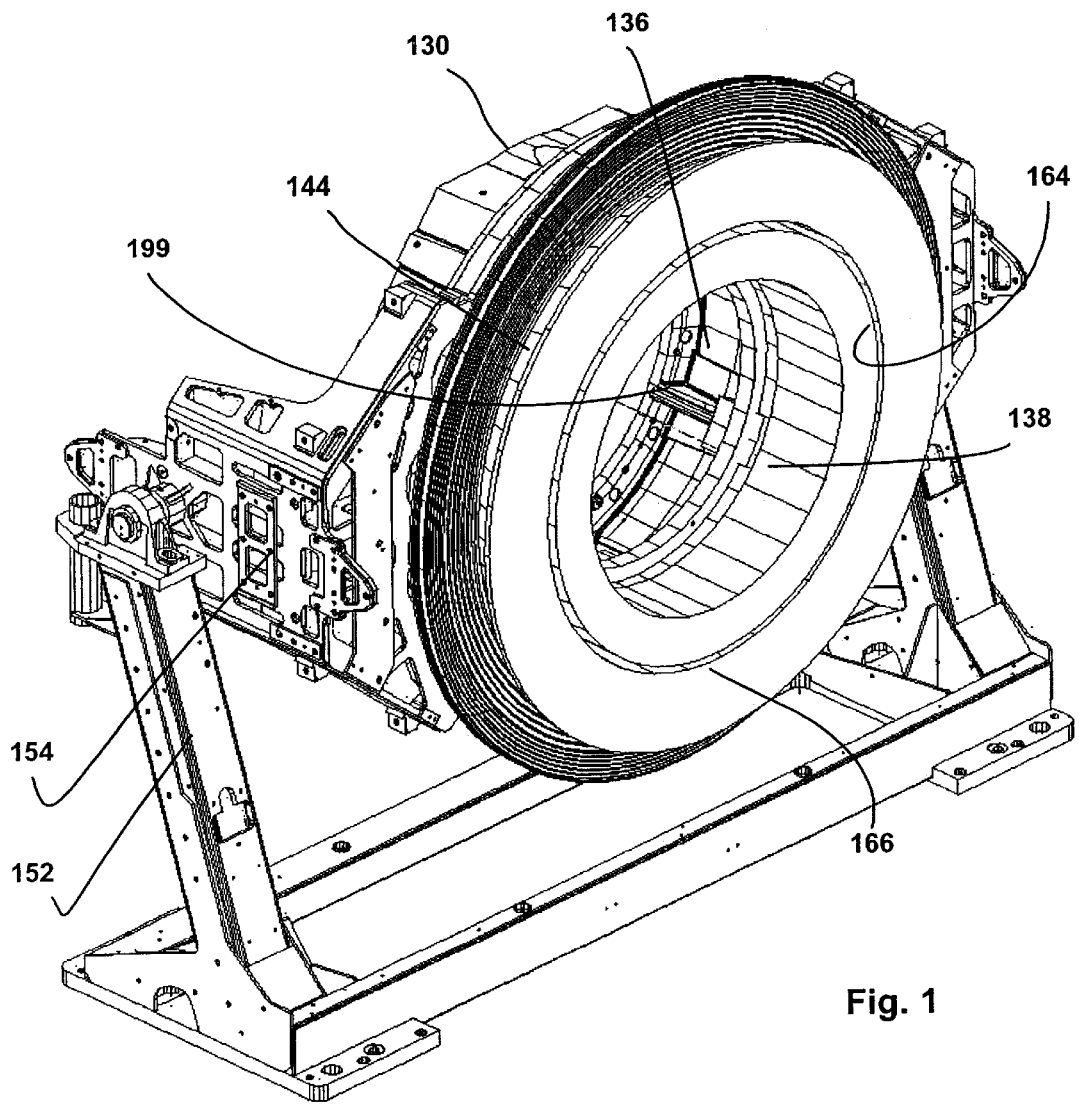
FIG. 1 is a schematic diagram illustrating a prior art dual CT-PET imaging system.

Referring now to the drawings wherein like reference characters represent similar components throughout the several views and, more specifically, referring to FIGS. 2, 3 and 4, the present invention will be described in the context of a dual CT-PET imaging system 110 including a support table 120, a CT imaging system 114 and a PET imaging system 116. Table 120 is supported on lockable wheels (not separately numbered) and is completely adjustable so that the height of a table support surface 112 can be raised and lowered and can be moved horizontally along a direction parallel to a translation axis 140 and also laterally with respect thereto.

CT imaging system 114 includes, among other things, a radiation source 124, a radiation detector 126 and a CT base support 130. Base support 130 is essentially a rigid annular member including front and rear ends 160 and 162, respectively, and forming an annular bore 164 therethrough. Source 124 and detector 126 are mounted to the front end 160 of support 130 on opposite sides of bore 164 so that source 124, when on, directs a radiation fan beam 128 toward detector 126. The beam 128 defines a CT imaging area also referred to hereinafter by numeral 128.

An annular slip-ring 166 is mounted to the rear end 162 of support 130 and cooperates with an annular track member 168 to mount and support the support 130 for rotation about translation axis 140 as will be explained in more detail below. Slip-rings like ring 166 are well known in the art and therefore ring 166 will not be explained here in detail. However, it should be noted that ring 166 facilitates providing power to source 124 and other electronics within support 130 and also facilitates data transfer from detector 126 and support 130 to other system components (not illustrated) such as data acquisition and archiving electronics.

Figure 3:
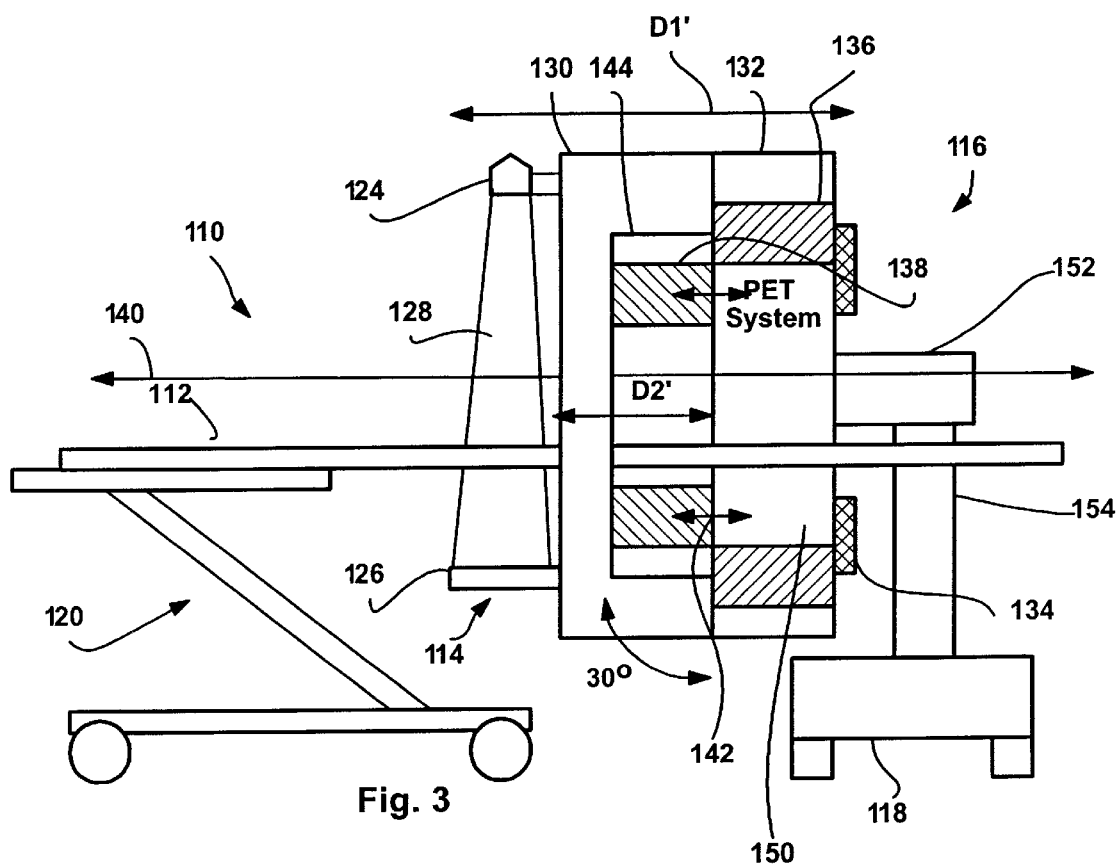
FIG. 3 is a schematic view like the view of FIG. 1, albeit illustrating the dual CT-PET imaging system of the present invention, portions of the schematic diagram illustrated in cross-section.

Referring in particular to FIG. 3, in cross-section, support 130 is essentially "C" shaped so as to define an annular parking space 170 that opens to rear end 162, slip-ring 166 essentially circumscribing the opening into parking space 170. The inside surface of support 130 defies a radius R1.

Figure 2:
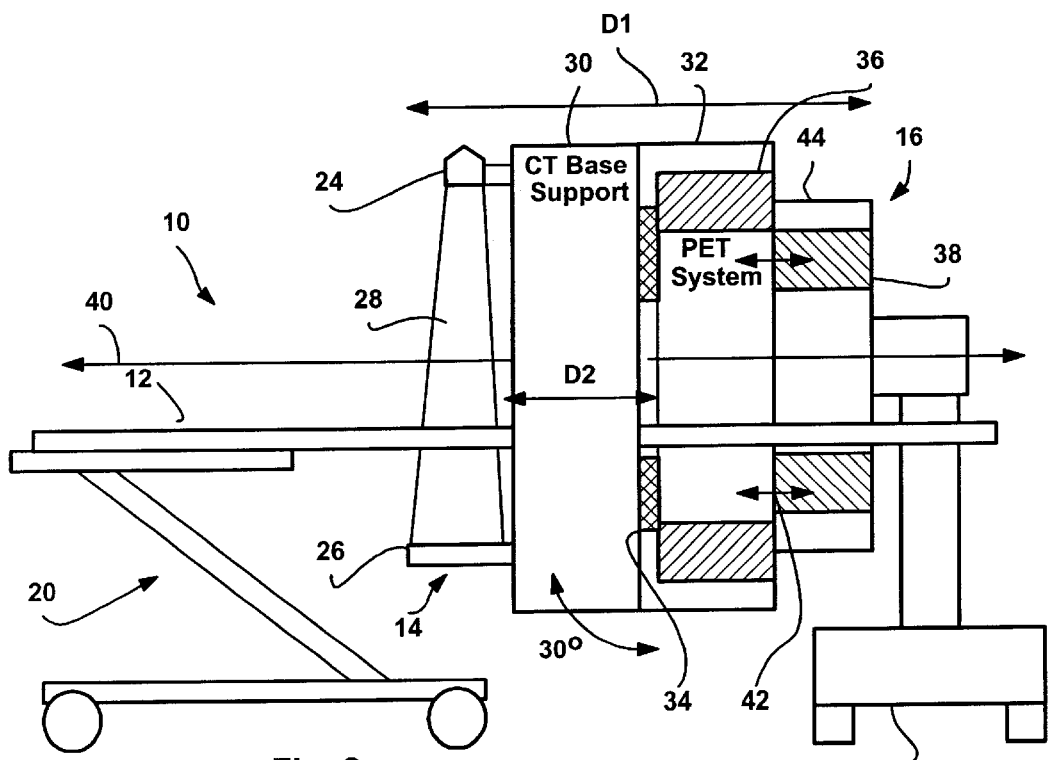
FIG. 2 is a perspective view of a dual CT-PET imaging system according to the present invention.

Referring to FIGS. 2, 3 and 4, PET system 116 includes an annular gantry 132, an annular PET detector 136, a collimator support 144 and a collimator 138. Gantry 132 includes front and rear ends (i.e., the front and rear ends of the PET system generally) 180 and 182, respectively, and also forms an annular gantry bore 174. Bore 174 has a radius (not illustrated) that is greater than the CT support radius 164 so that, as other PET system components (e.g., the detector, the collimator, etc.) are positioned within bore 174, the resulting reduced radius bore is essentially identical to the support bore 164.

PET detector 136 has an annular shape and is sized so as to be received within gantry bore 174. Detector 136 forms an internal annular detector bore 176.

Collimator support 144 also has an annular shape defined by concentric internal and external surfaces 188, 190, respectively. External surface 190 is essentially annular and defies a radius R2 that is less than the radius R1 of support 130. Support 144 is mounted to the front end 180 of gantry 132 so as to circumscribe detector bore 176. To this end, bore 188 is formed so as to have a radius that is essentially identical to the radius of detector bore 176. As best illustrated in FIG. 2, three rails 199 (only one shown) are provided within the collimator support bore and the PET detector bore 176. The rails 199 are equi-spaced about the bores and extend in a direction parallel to translation axis 140.

Referring still to FIG. 4 and also to FIG. 1, collimator 138 has an annular shape and is sized so as to fit within and mount to PET detector bore 176. More specifically, collimator 138 is received on rails 199 that facilitate easy movement between a first position as illustrated in FIG. 4 where the collimator 138 is positioned within detector 136 and a second position illustrated in FIG. 3 where collimator 138 is within and supported by collimator support 144 outside detector 138. Any of several different configurations may be used to mount the collimator 138 to the rails for movement.

Referring still to FIG. 4, in addition to support 144, a slip-ring receiving track 168 is also mounted to the front end 180 of gantry 132. As well known in the industry, track 168 receives slip-ring 166 and cooperates therewith to provide power and control signals to source 124, to provide power to a motor (not illustrated) for rotating CT support 130 about axis 140 and to receive data from detector 126.

Referring still to FIG. 4, an annular radiation shield 134 is mounted to the rear end 182 of the PET detector 136. Shield 134 forms an annular opening (not separately numbered) that has a radius essentially the same as the radius of collimator 138.

Referring still to FIGS. 2, 3 and 4, when assembled to form a dual CT-PET imaging system, all of the components described are mounted to each other so that corresponding bores and openings are all aligned along translation axis 140 as illustrated. In addition, CT support 130 is mounted to the front end 180 of detector/gantry 136/132 such that collimator support 144 extends into parking space 170. Thus, when passing through system 110 beginning at the CT end of the dual system, a patient first passes through the CT imaging beam 128, then through support bore 164, then through the remainder of support 130 and collimator support 144, then through PET detector 136 and finally through radiation shield 134.

The dual imaging configuration including systems 114 and 116 is mounted to a configuration support including a base 118, upright extensions 154 (see FIG. 2) and horizontal extensions 152. Extensions 154 extend upward from base 118 and extensions 152 extends laterally from a top end of extensions 154. Gantry 132 is mounted to distall ends of extensions 154. Extensions 152 are pivotal about an axis (not illustrated) that passes through the connections between extensions 152 and 154 so that systems 114 and 116 can pivot thereabout to facilitate various angles.

Referring now to FIGS. 2 and 3, it should be appreciated that the overall length D1' of the dual system bore in the inventive configuration (i.e., FIG. 3) is reduced when compared to the overall length D1 of the bore in the prior art systems as support 144 is positioned within the CT base support in the previously unused parking space 170. In essence, the overall dual system bore length is reduced by approximately the length of the collimator and collimator support bores. In addition, comparing FIGS. 2 and 3, it should also be appreciated that by moving the radiation shield 134 from between the CT and PET imaging areas to the side of the PET detector 136 opposite the CT imaging area 128, the space between the CT and PET imaging areas is reduced by at least the width of the radiation shield 134.

It should be understood that the methods and apparatuses described above are only exemplary and do not limit the scope of the invention, and that various modifications could be made by those skilled in the art that would fall under the scope of the invention.

To apprise the public of the scope of this invention, the following claims are made:

What is claimed is:

1. A combined CT-PET imaging system comprising:
    a CT source;
    a CT detector;
    a CT support having front and rear oppositely facing ends, the source and detector mounted to the front end so as to oppose each other and for rotation about a translation axis passing through a CT imaging area, the CT support also forming a parking space axially adjacent along the translation axis to the CT imaging area;
    an annular PET detector having front and rear oppositely facing ends, the PET detector positioned such that the front end of the PET detector is adjacent the rear end of the CT support;
    an annular collimator mounted to the PET detector for movement between a first position wherein the collimator is disposed within the PET detector and a second position wherein the collimator is outside the PET detector and at least partially within the parking space.

2. The apparatus of claim 1 further including a collimator support mounted to the PET detector and extending from the front end at least part way into the parking space and wherein the collimator is mounted to the collimator support for movement.

3. The apparatus of claim 2 wherein the collimator support is mounted to the front end of the PET detector.

4. The apparatus of claim 2 wherein the support includes rails and the collimator is mounted for movement along the rails.

5. The apparatus of claim 2 further including a radiation shield mounted to the second end of the PET detector.

6. The apparatus of claim 1 wherein the PET detector is mounted to the second end of the CT support.

7. The apparatus of claim 1 wherein the collimator includes front and rear ends and wherein, when the collimator is in the second position, the rear end of the collimator is proximate the front end of the PET detector such that the rear end of the collimator forms a radiation shield on the front end of the PET detector.

8. A combined CT-PET imaging system comprising:

a CT source;

a CT detector;

a CT support having front and rear oppositely facing ends, the source and detector mounted to the front end so as to oppose each other and for rotation about a translation axis passing through a CT imaging area, the CT support;

an annular PET detector having front and rear oppositely facing ends, the PET detector mounted to the CT support such that the front end of the PET detector is adjacent the rear end of the CT support;

an annular collimator mounted to the PET detector for movement between a first position wherein the collimator is disposed within the PET detector and a second position wherein the collimator is outside the PET detector; and a radiation shield mounted to the rear end of the PET detector opposite the CT support such that the shield is adjacent the collimator when the collimator is in the first position.

9. The apparatus of claim 8 wherein the CT support also forms a parking space axially adjacent along the translation axis to the CT imaging area and, wherein, when the collimator is in the second position, the collimator at least partially within the parking space.

10. A combined CT-PET imaging system comprising:

means for generating an X-ray fan beam;

means for detecting an X-ray fan beam;

means for supporting the means for generating and means for detecting, the means for supporting having front and rear oppositely facing ends, the means for generating and means for detecting mounted to the front end so as to oppose each other and for rotation about a translation axis passing through a CT imaging area, the means for supporting also forming a parking space axially adjacent along the translation axis to the CT imaging area;

means for PET detecting having front and rear oppositely facing ends, the means for PET detecting positioned such that the front end of the means for PET detecting is adjacent the rear end of the means for supporting;

means for collimating mounted to the means for PET detecting for movement between a first position wherein the means for collimating is disposed within the means for PET detecting and a second position wherein the means for collimating is outside the means for PET detecting and at least partially within the parking space.

11. The apparatus of claim 10 further including a means for supporting the collimator mounted to the front end of the means for PET detecting and extending at least part way into the parking space and wherein the means for collimating is mounted to the means for supporting the collimator for movement.

12. The apparatus of claim 11 further including a means for blocking radiation mounted to the rear end of the means for PET detecting to block radiation from the space to the rear end side of the means for PET detecting.

13. The apparatus of claim 11 further including a means for motivating linked to the means for collimating for moving the means for collimating between the first and second positions.

14. The apparatus of claim 10 wherein the means for PET detecting is mounted to the rear end of the means for supporting.

15. The apparatus of claim 10 wherein the means for collimating includes front and rear ends and wherein, when the means for collimating is in the second position, the rear end of the means for collimating is proximate the front end of the means for PET detecting such that the rear end of the collimating means forms a means for blocking radiation on the front end of the means for PET detecting.

16. A combined CT-PET imaging system comprising:

a CT source;

a CT support having front and rear oppositely facing ends, the source and detector mounted to the front end so as to oppose each other and for rotation about a translation axis passing through a CT imaging area, the CT support also forming a parking space axially adjacent along the translation axis to the CT imaging area;

an annular PET detector having front and rear oppositely facing ends, the PET detector positioned such that the front end of the PET detector is adjacent the rear end of the CT support;

an annular radiation shield mounted to the rear end of the PET detector and extending radially inwardly further than the PET detector toward the translation axis so as to block radiation from being detected by the detector from the rear end side of the PET detector;

a collimator support mounted to the PET detector and extending from the front end of the PET detector and at least part way into the parking space;

an annular collimator having front and rear ends and mounted to the collimator support for movement between a first position wherein the collimator is disposed within the PET detector and the rear end of the collimator is adjacent the shield and a second position wherein the collimator is outside the PET detector and at least partially within the parking space and wherein the rear end of the collimator is proximate the front end of the PET detector such that the rear end of the collimator forms a radiation shield on the front end of the PET detector.

17. The apparatus of claim 16 further including a motivator linked to the collimator for moving the collimator between the first and second positions.

18. The apparatus of claim 16 wherein the collimator support is mounted to the front end of the PET detector.

19. The apparatus of claim 16 wherein the collimator support is essentially positioned within the parking space.

* * * * *